United States Patent [19]

Tisdale et al.

[11] Patent Number: 5,457,130
[45] Date of Patent: Oct. 10, 1995

[54] EICOSAPENTAENOIC ACID USED TO TREAT CACHEXIA

[75] Inventors: Michael J. Tisdale, Claverdon; Susan A. Beck, Willenhall, both of United Kingdom

[73] Assignee: Cancer Research Campaign Technology Limited, London, England

[21] Appl. No.: 280,244

[22] Filed: Jul. 25, 1994

Related U.S. Application Data

[63] Continuation of Ser. No. 938,534, Sep. 2, 1992, abandoned, which is a continuation of Ser. No. 548,894, filed as PCT/GB90/00425, Mar. 20, 1990, abandoned.

[30] Foreign Application Priority Data

Mar. 20, 1989 [GB] United Kingdom .................. 890636

[51] Int. Cl.$^6$ .......................... A61K 31/19; A61K 31/20
[52] U.S. Cl. .......................... 514/560; 514/557; 514/573
[58] Field of Search .......................... 514/560, 557, 514/573

[56] References Cited

U.S. PATENT DOCUMENTS

| | | | |
|---|---|---|---|
| 4,835,183 | 5/1989 | Yamatsu et al. | 514/560 |
| 4,954,525 | 9/1990 | Yamatsu et al. | 514/549 |
| 4,960,795 | 10/1990 | Salte et al. | 514/560 |

FOREIGN PATENT DOCUMENTS

| | | |
|---|---|---|
| 8319333 | 9/1983 | Australia . |
| 122597 | 8/1987 | Canada . |
| 175468 | 8/1984 | European Pat. Off. . |
| 0378824 | 7/1990 | European Pat. Off. . |
| 3303925 | 12/1988 | Japan . |
| 2134782 | 8/1984 | United Kingdom . |
| 2223943 | 4/1990 | United Kingdom . |
| 0385859 | 9/1990 | United Kingdom . |

OTHER PUBLICATIONS

Laustiola et al, Biochimica et Biophysica Acta, vol. 889, 1986, Elsevier Science Publishers B.V.
Karmall et al, J.N.C.J., vol. 73, No. 2, Aug., 1984.
Begin et al, Prostaglandins Leukotrienes and Medicine, vol. 19, 1985.
Booyens et al, IRCS Medical Science, vol. 14, No. 4, 1986.
Steven et al, J. Enzym. Inhib., vol. 1, No. 2, 1987.

*Primary Examiner*—Theodore J. Criares
*Attorney, Agent, or Firm*—Cushman Darby & Cushman

[57] ABSTRACT

The use of the omega-3 polyunsaturated fatty acid eicosapentaenoic acid or EPA, preferably substantially free of any other polyunsaturated fatty acids, is disclosed for making up medical preparations or compositions for the treatment of cachexia by inhibiting lipolytic activity of biologically active lipolytic agents present in body fluids and the activity of the enzyme guanidinobenzoatase, as well as for reducing abnormal cAMP levels in cells of adipose tissue in mammals, produced by lipolytic or fat mobilizing substances.

4 Claims, 7 Drawing Sheets

A. Control cells only
B. 0.331mM EPA
C. 50μl factor (0.082 μmoles glycerol released/10⁵adipocytes/2hr)
D. 50μl factor + 0.331mM EPA
E. 25units ACTH
F. 25units ACTH + 0.331mM EPA
G. 0.165mM Salbutamol
H. 0.165mM Salbutamol + 0.331mM EPA

EICOSAPENTAENOIC ACID USED TO TREAT CACHEXIA

This is a continuation of application Ser. No. 07/938,534, filed on Sep. 2, 1992, which was abandoned, which is a continuation of application Ser. No. 07/548,894, filed as PCT/GB90/00425, Mar. 20, 1990, which was abandoned.

This invention relates to the omega-3 polyunsaturated fatty acid 5,8,11,14,17-eicosapentaenoic acid (herein referred to shortly as EPA, which term is to be understood as including also physiologically functional derivatives thereof, e.g. salts or esters), and to use in medicine of this compound for providing an active therapeutic agent. EPA is known to occur naturally as one of the several fatty acid constituents of marine oil, commonly called "fish oil".

BACKGROUND

The present invention has arisen out of experimental studies investigating a newly-identified biologically active substance having a high lipolytic activity which seems to be specifically associated with a range of malignant rumours, especially cachexia-inducing tumours, in animals and in humans, as disclosed for example in the specification of our European patent application No. 89302740.9 (EU0335550) of which the content is incorporated herein by reference. During the course of these studies, EPA was found to be an effective antagonist or inhibitor of this so-called lipolytic factor; it was also found to be effective in depressing an abnormal elevated level of cyclic adenylic acid (cAMP) produced in adipose tissue cells (adipocytes) by this so-called lipolytic factor or by other known lipolytically active substances, as evidenced by experiments conducted using mouse adipose tissue cell preparations. These are newly-identified properties of EPA not hitherto reported before the priority date of the present application.

SUMMARY OF THE INVENTION

The present invention is based on the above findings and also on the further finding that administration of EPA is effective in vivo in suppressing the symptoms of cachexia, especially cancer cachexia, and/or in inhibiting or reducing rumour growth whereby it can provide a useful active therapeutic agent for treatment of these conditions. These effects, it is believed, are related at least in part to in vivo activity peculiar to EPA in inhibiting the newly-identified lipolytic factor and in reducing abnormal elevated cAMP levels in adipose tissue cells produced by this or by other lipolytic agents. It may also be related to inhibition of proteolytic activity which has been noted in respect of skeletal muscle in some instances of rumour growth.

It has also been found that EPA can have an inhibitory effect on guanidinobenzoatase which, it is believed, may promote an effect of EPA in reducing invasive and metastatic activities of malignant rumour cells.

Thus, according to one aspect of the present invention, 5,8,11,14,17-eicosapentaenoic acid or a physiologically functional derivative thereof, e.g. a salt or ester, herein collectively designated EPA, is used to make a medical preparation or medicament for the treatment of cachexia and/or malignant rumours in mammals.

Also, according to the invention, EPA as specified above is used to make a medical preparation or medicament for therapeutic treatment to reduce abnormal cAMP levels in cells of adipose tissue in mammals produced by a lipolytic or fat mobilising substance present in body fluids or the circulatory system.

The invention also comprises the use of EPA as specified above for the manufacture of a medical preparation or medicament for therapeutic treatment to inhibit lipolytic activity of biologically active lipolytic agents present in body fluids in mammals and/or activity of the enzyme guanidinobenzoatase associated with rumour cells and cells capable of migration in mammals.

In carrying out the invention, in general an effective anti-cachectic and/or antitumour amount of the EPA, or an effective amount of EPA for reducing an abnormal elevated level of cAMP in adipose tissue cells produced by a lipolytic or fat mobilising substance present in the body fluids or circulatory system of a mammal to be treated, will be made up as a pharmaceutical formulation ready for administration in any suitable manner, for example orally, parenterally (including subcutaneously, intramuscularly and intravenously), or topically. Such formulations may be presented in unit dosage form and may comprise a pharmaceutical composition, prepared by any of the methods well known in the art of pharmacy, in which the active EPA component is in intimate association or admixture with at least one other ingredient providing a compatible pharmaceutically acceptable carrier, diluent or excipient. Alternatively, such formulations may comprise a protective envelope of compatible or relatively inert pharmaceutically acceptable material within which is contained the active EPA component in the form of concentrated or pure EPA without association or admixture with any other ingredients.

Formulations of the present invention suitable for oral administration may be presented as discrete units such as capsules, cachets, tablets or lozenges, each containing a predetermined amount of the active EPA component, with capsules being a preferred type of formulation for providing the most effective means of oral delivery. For parenteral administration the formulations may comprise sterile liquid preparations of a predetermined amount of the active EPA component contained in sealed ampoules ready for use.

In a further alternative definition the invention, from one aspect, may also be expressed as providing a composition for inhibiting lipolytic activity of biologically active lipolytic agents present in body fluids in mammals and/or for inhibiting the enzyme guandinobenzoatase associated with rumour cells and with cells capable of migration in mammals, characterised in that the composition comprises an effective inhibiting amount of EPA (as herein defined) together with a compatible pharmaceutically acceptable material or carrier.

Preferably, the EPA used for making the medical preparations, medicaments or compositions in accordance with the invention is of at least about 90% purity and will contain no more than minimal or pharmaceutically insignificant amounts of any other polyunsaturated fatty acids. A purity of more than 90% is recommended with the highest commercially available grade (about 95% purity), which is substantially free of any other polyunsaturated fatty acids, being the most preferred material.

Although EPA of high purity readily oxidises and is an inherently unstable compound under normal ambient conditions in the presence of air such that it usually requires to be stored out of sunlight at a low temperature under an atmosphere of nitrogen, difficulties in handling can be minimized by observing precautionary measures well known in the art. It will normally be protected from contact with air and sunlight in the pharmaceutical formulations into which it is made up for therapeutic use and such formulations may be kept stored at low temperatures until required for use.

By way of further background explanation and description of the invention, illustrative examples are hereinafter presented of investigations made and results obtained in the development of the invention, from which the skilled person in the art will more readily be able to appreciate the nature thereof and to put the invention into practical effect.

BRIEF DESCRIPTION OF THE DRAWINGS

In the accompanying drawings.

MORE DETAILED DESCRIPTION

In some preliminary experiments using mice, evidence was first obtained suggesting that EPA could inhibit the growth in vivo of at least two different rumours, designated MAC16 and MAC13 respectively, belonging to an established series (MAC) of chemically induced, transplantable colon adenocarcinomas (see for example Cowen et al (1980), *JNCI*, 64, 675–681), and could reduce the weight loss or cachexia associated with the MAC16 rumour. The MAC16 rumour is a cachexia-inducing rumour associated with high levels of lipolytic activity and also with proteolytic activity; the MAC13 is (at least in mice) a non-cachexia inducing colon adenocarcinoma (albeit extracts thereof do show a certain level of lipolytic activity). Subsequent studies in vivo with the MAC16 rumour further indicated that the reduction in weight loss and inhibition of the tumour-associated lipolytic activity referred to above, as well as the rumour growth inhibition, was a dose related effect. However, the anticachectic effect of EPA appears, somewhat surprisingly, to exceed the antitumour effect.

During the course of continuing investigations of the newly identified so-called lipolytic factor, derived from the above-mentioned tumours as disclosed in our aforesaid European patent application No. 89302740.9 (EU0335550), a series of in vitro experiments was conducted to screen a range of various compounds, including EPA, for possible activity as inhibitors or antagonists to the lipolytic factor. In general, in these experiments the compounds to be tested were added to extracts from MAC16 rumours and incubated with freshly prepared adipocytes from mouse epididymal adipose tissue for 2 hrs. The lipolytic activity, or reduction thereof, was then determined by measuring the glycerol release using an enzyme assay that results in a production of NAD (nicotinamide adenine dinucleotide) from the reduced form NADH, the amount of NAD corresponding to the amount of glycerol present. The NAD was measured spectrophotometrically as a decrease in absorption at 340 nm.

More specific details of the experimental procedures in these inhibition studies are summarised below:

1. Preparation of extracts from MAC16 tumours. MAC16 rumours from NMRI mice that had lost up to one third of their original body weight, were homogenised in Krebs-Ringer buffer at a concentration of 0.2 g/ml. The homogenate was then centrifuged and the supernatant used for inhibition studies.

2. Preparation of adipocytes Fat pads were removed from 2 mice for the assay of each batch of 10 samples. 1 ml of collagenase solution in Krebs buffer (2 mg/ml) was added to the fat pads from 1 mouse which were then finely chopped prior to incubation for 2 hr at 37° C. After 2 hr the adipocytes were pooled, washed three times in Krebs buffer, and then counted to obtain a concentration of $1.5–2.0\times10^5$ adipocytes per ml.

The experiment was set up as follows. 100 µl tumour extract+1 ml fat cells Compound to be screened+1 ml fat cells 100 µl rumour and compound+1 ml fat cells Each compound was tested at increasing concentrations and all samples were prepared and processed in duplicate.

The samples were gassed for 2 min with 95% $O_2$, 5% $CO_2$ mixture, mixed and incubated for 2 hr at 37° C. After 2 hr, 0.5 ml from each sample was then assayed for glycerol content.

Figure 1:
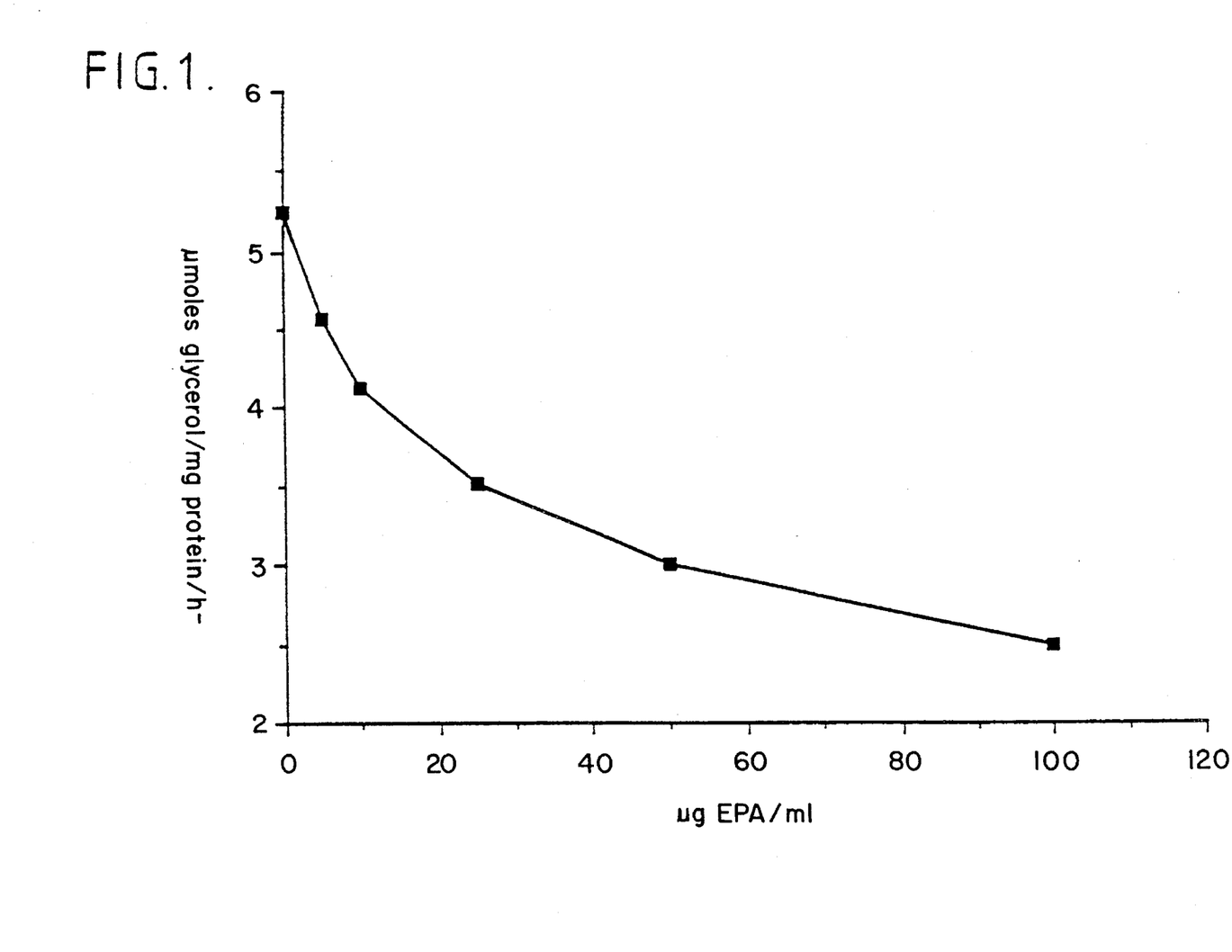
FIGS. 1 and 2 are diagrams showing the effect of EPA on lipolytic activity associated with MAC16 rumour extracts.
Figure 2:
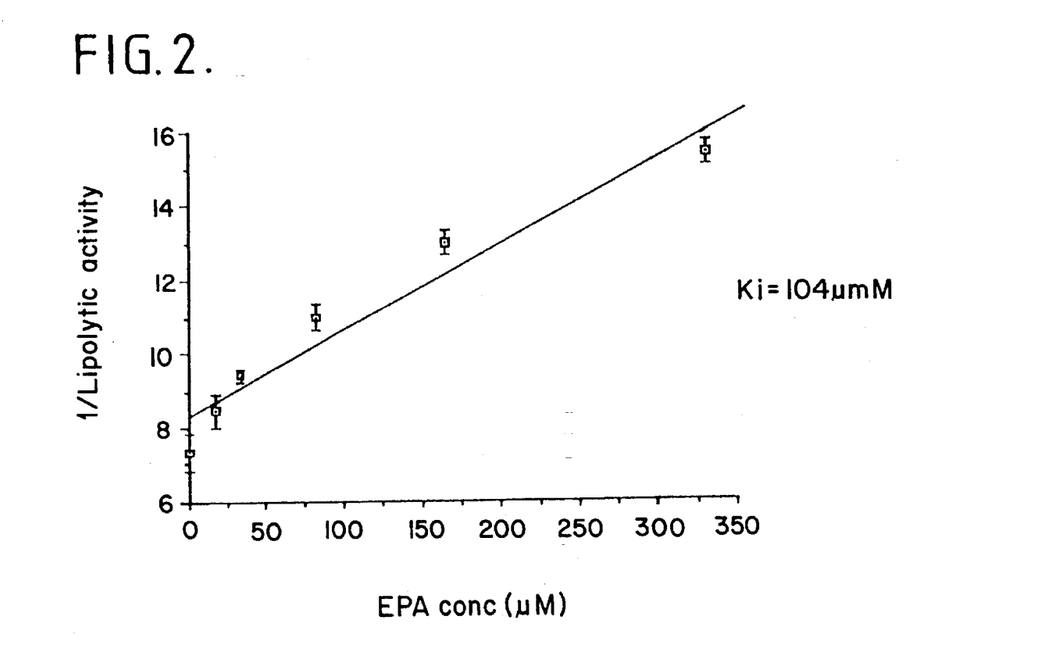

These experiments confirmed that EPA at a sufficient dosage has a strong inhibitory effect on the lipolytic activity of the lipolytic factor in the tumour extracts, as illustrated for example by FIG. 1 of the accompanying drawings. This diagram shows the results obtained using EPA in one set of the above experiments and it also clearly indicates the dose dependence nature of the effect. In FIG. 2, the same results are presented as a Dixon plot. Lipolytic activity is expressed as µmol glycerol released from the murine epididymal adipocytes per mg protein per hr. Results are expressed as mean±S. E. M and the number of experiments performed was 3 to 4.

Similar tests on a range of compounds, including other related polyunsaturated fatty acids, failed to indicate any significant inhibition of the lipolytic factor in the tumour extracts by Linolenic acid, Octadocatetraenoic acid, Trans-3-Hexenoic acid, Trans 2-Hexenoic acid, Cis-3-Hexen-1-ol, 3-Octenoic acid, Linoleic acid, Eicosatrienoic acid, Arachidonic acid, Palmitoleic acid, Nicotinic acid, Adenosine and Inosine. As will hereinafter appear, docosahexaenoic acid also appears not be act as an inhibitor of the activity of this rumour lipid mobilising agent or lipolytic factor.

Figure 3:
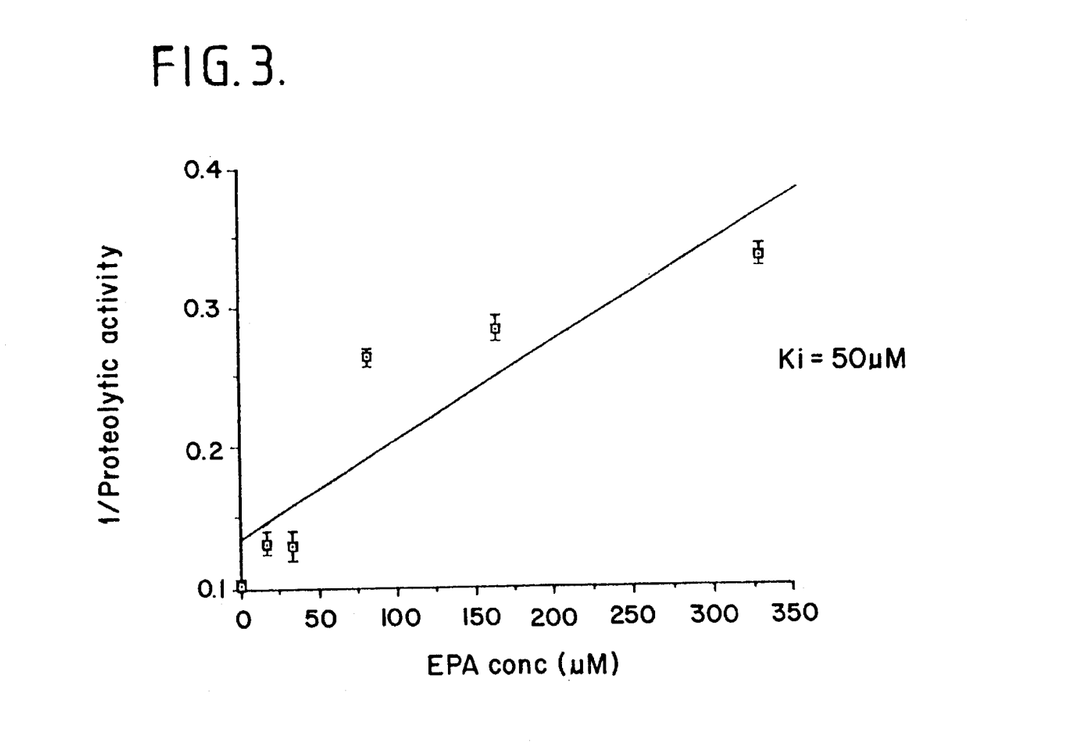
FIG. 3 is a diagram showing the effect of EPA on proteolytic activity associated with MAC16 rumour extracts.

In addition, in similar experiments wherein extracts of MAC16 tumours were incubated with mouse diaphragm, EPA was found to inhibit the proteolytic activity, as shown for example in FIG. 3 in which the results of typical experiments are again presented as a Dixon plot. In this diagram, proteolytic activity of the tumour extracts is expressed in terms of nmoles total amino acid released per gram diaphragm per mg protein per 2 hr and are corrected for spontaneous amino acid release. Results are expressed as mean±S. E. M and the number of experiments performed was 3 to 4.

Figure 4:
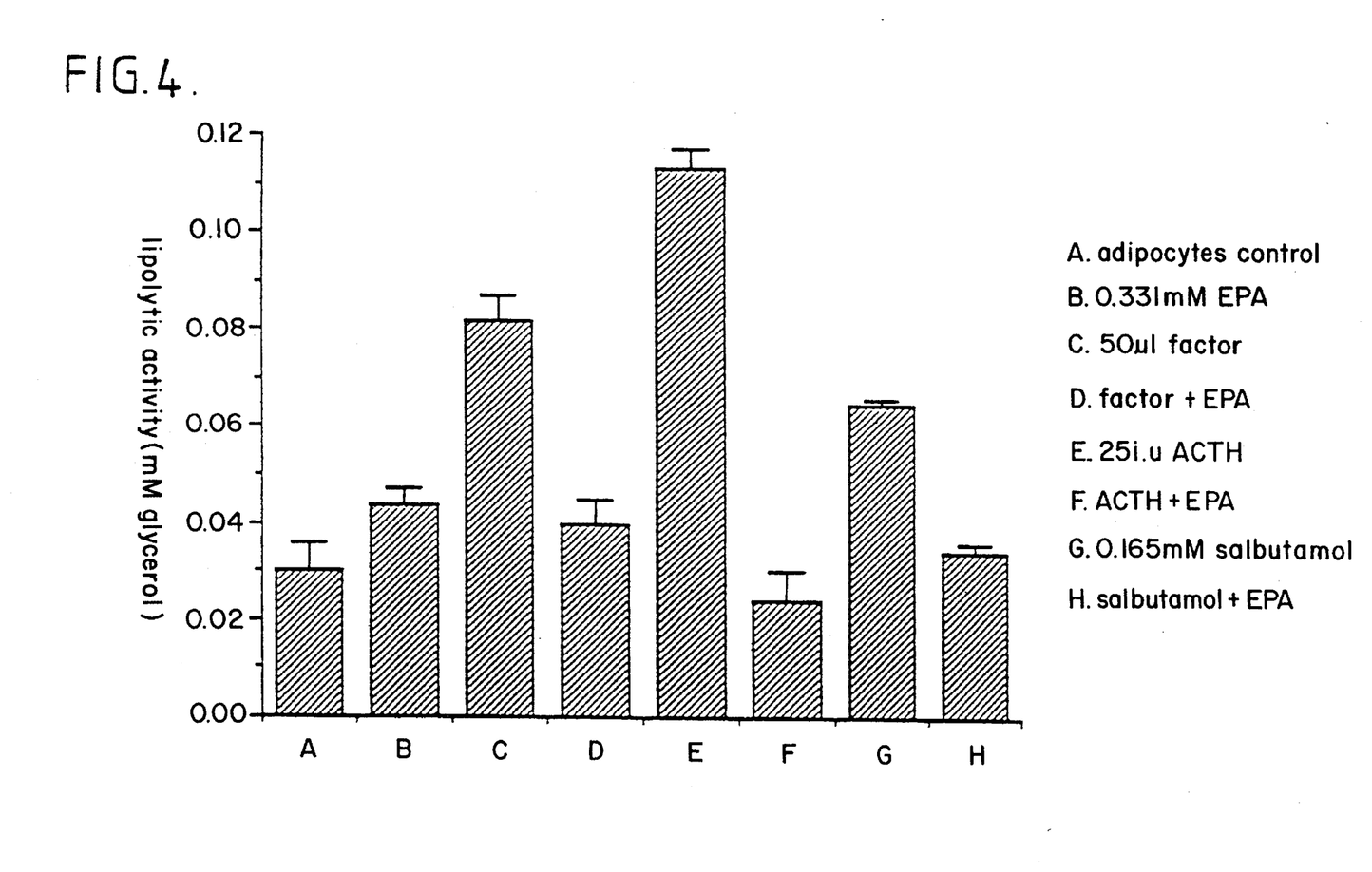
FIG. 4 is a bar chart diagram showing the effect of EPA on the activity of several different lipolytic agents.

In a further series of similar experiments, EPA was found to act as an effective inhibitor not only of the lipolytic factor from the tumour extracts referred to above, but also of some other substances that are known to function as biologically active lipolytic agents. These included ACTH (the lipase activating adrenocorticotropic hormone) and Salbutamol, the effects being illustrated in FIG. 4 of the accompanying drawings which is a bar chart diagram showing the relative levels of lipolytic activity detected under comparable conditions for the various test samples enumerated.

Figure 5:
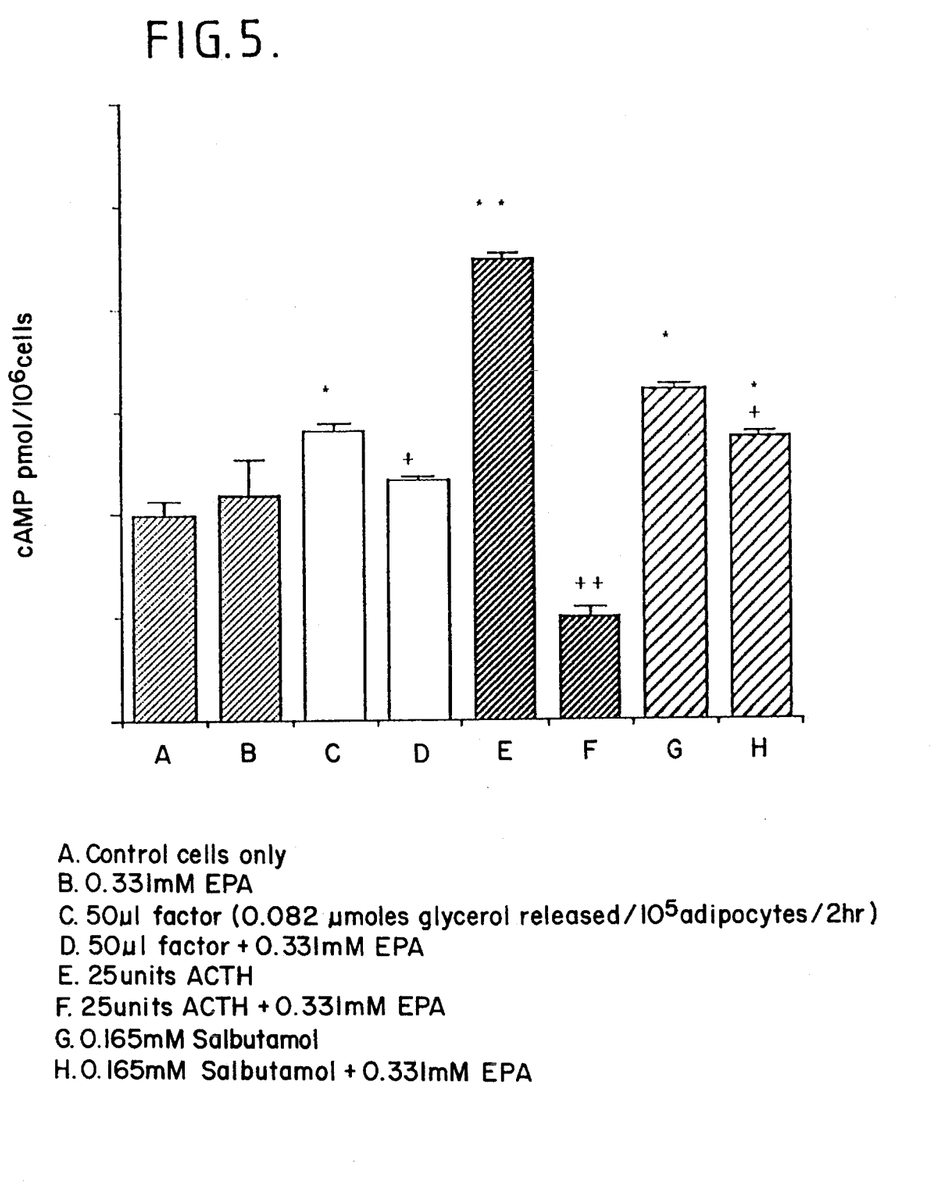
FIG. 5 is a similar bar chart diagram showing the effect of EPA on the level of cAMP in fat cells or adipocytes during incubation with the different lipolytic agents referred to in FIG. 4.

In the course of these latter experiments, tests were also carried out to measure (by known techniques) the level of cyclic adenylic acid (cAMP) in the fat cells or adipocytes during the period of incubation with the various lipolytic agents, both in the presence of and without the presence of EPA. The results, after a 10 minute incubation period, are presented in the bar chart diagram of FIG. 5 of the accompanying drawings which should be compared with FIG. 4. The results in FIGURE are expressed as the mean±S. E. M of 3 to 4 experiments. It will be seen that each of the three specific lipolytic agents tested, when present on its own and lipolytically most active, gives rise to an abnormal elevated level of cAMP in the cells, but this elevated level is depressed in the presence of EPA. This suggests that normally, like many hormones, these lipolytic agents bind to specific receptor sites on the membrane of the fat cells or adipocytes concerned and act to bring about a modification of the intracellular level of cAMP which is known to act as a so-called secondary hormone that regulates the activity of enzyme systems within the cell. The indications are that the EPA interferes with and inhibits this effect, acting specifically somewhere in the adenylate cyclase cascade to inhibit the production of cAMP in response to lipolytic stimuli, perhaps by itself binding to and blocking the receptor sites involved. Again, this property has been found to be unique to EPA and is not shown by other polyunsaturated fatty acids.

Figure 6:
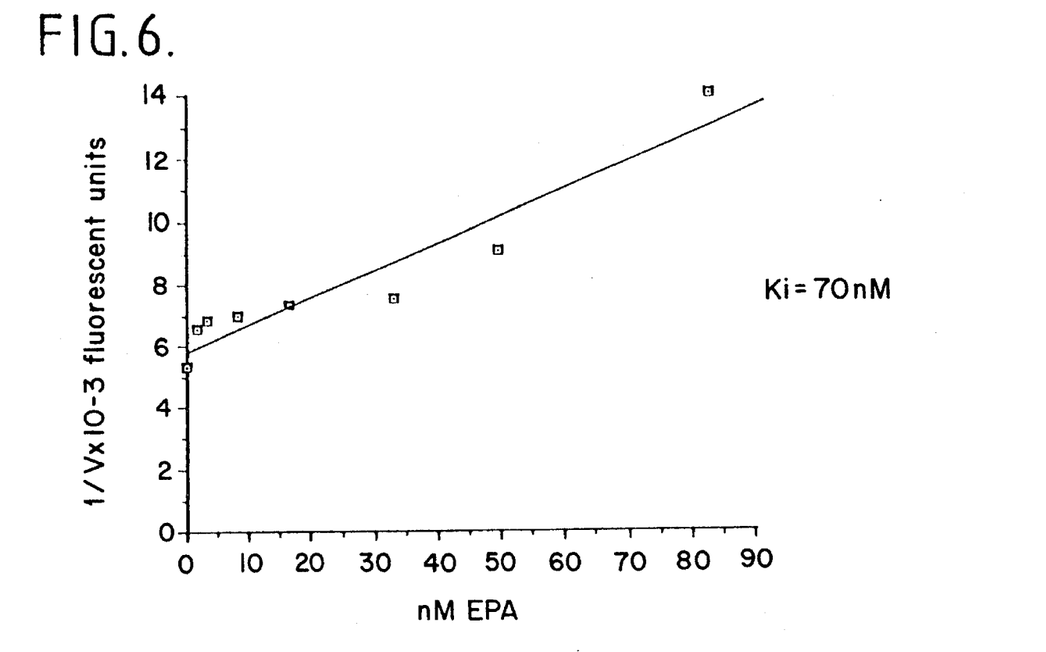
FIG. 6 is a diagram showing the inhibition effect of EPA on guanidinobenzoatase.

In addition, as illustrated by the Dixon plot of results shown in FIG. 6, EPA has been found to be a highly effective inhibitor of the enzyme guanidino-benzoatase which is a trypsin-like enzyme associated with tumour cells and cells capable of migration and which, it has been suggested, may play a role in tumour metastasis. In deriving the results shown in FIG. 6, enzyme activity was determined by the release of the fluorogenic product methyl umbelliferone from 4-methylumbelliferyl-p-guanidinobenzoate by 1µl of NMRI mouse serum. The inhibitor was added to the enzyme together with the substrate and the decrease of fluorescence at 446 nm was determined. In this property EPA is again also unique in that it appears to be the only fatty acid capable of effectively inhibiting guanidinobenzoatase.

Figure 7:
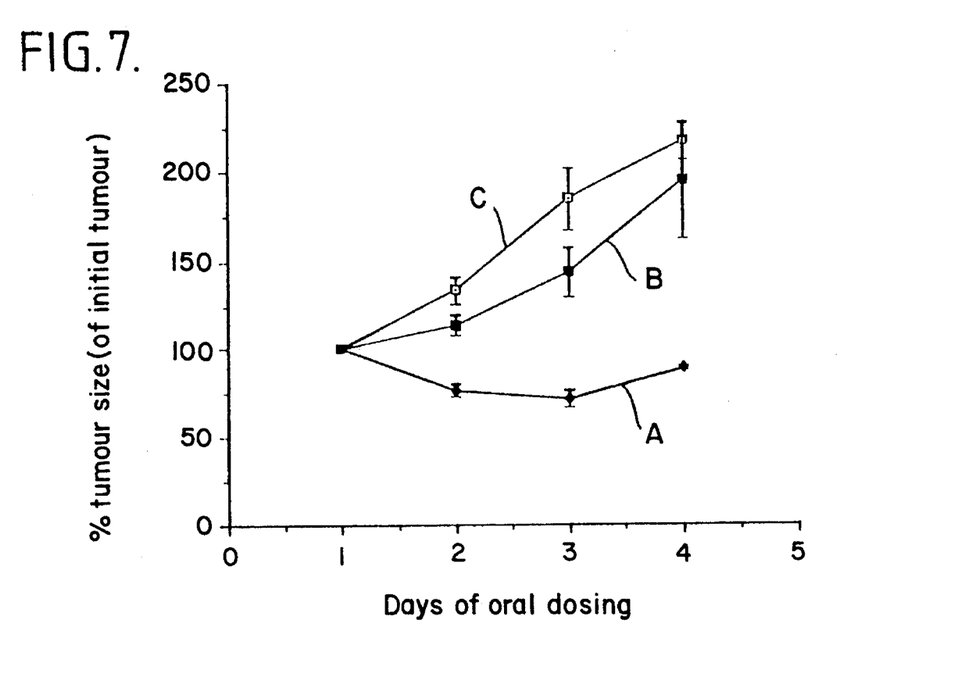
FIG. 7 is a diagram showing the effect of oral dosing with EPA on the growth of MAC16 adenocarcinoma in female NMRI mice.

In continuing in vivo experiments, it has been found that the pure EPA is surprisingly more effective as a therapeutic agent than had been anticipated and also it appears to have a very low toxicity. We have compared oral dosing of 95% pure EPA in the form of the triglyceride ester (obtained from Peninsula Laboratories, Merseyside, United Kingdom) with linoleic acid in mice bearing the MAC16 adenocarcinoma at a dose of 5 g kg$^{-1}$. No toxicity or other adverse effects were noted and the results in FIG. 7 show EPA at this dose level to produce an extensive growth delay. In obtaining these results, mice (20 g weight) were dosed orally with either 100 µl EPA/day/mouse (A), 100 µl linoleic acid/day/mouse (B) or 100 µl 0.9% saline/day/mouse (C). The experiment was initiated 14 days after rumour transplantation when the rumours became palpable (average initial rumour volume= 176±23 mm$^3$). Tumour volumes were measured daily and recorded as a percentage of the rumour volume prior to oral dosing. Results are expressed as the mean S. E. M.

Figure 8:
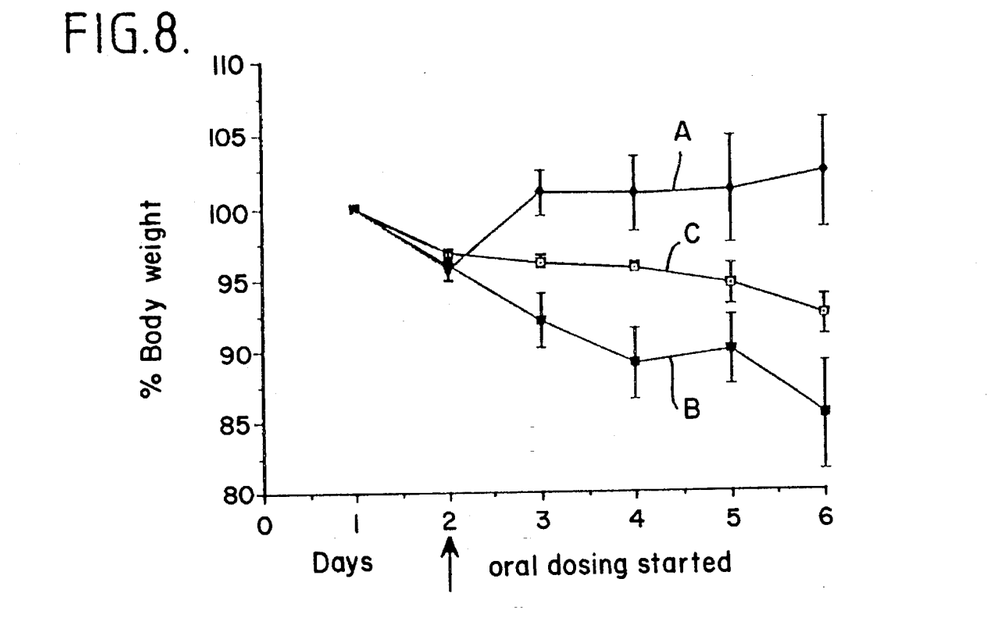
FIG. 8 is a similar diagram showing the effect of oral dosing with EPA on body weight of female NMRI mince bearing the MAC16 rumour.

The effect of the fatty acids on host body weight is shown in FIG. 8. Again mice (20 g) were dosed orally with either 100 µ EPA/day/mouse (A), 100 µl linoleic acid/day/mouse (B) or 100 µl 0.9% saline/day/mouse (C). Treatment was initiated 14 days after rumour transplantation when weight loss became apparent (average weight loss 5%). In this case, body weights were measured daily and recorded as a percentage of the body weight prior to oral dosing, the results again being expressed as the mean±S. E. M. There was no significant difference in food and water intake. As will be seen, the results show EPA also effectively blocked the cachectic effect of the rumour whereas linoleic acid at an equivalent dose level had an enhancing effect.

Figure 9:
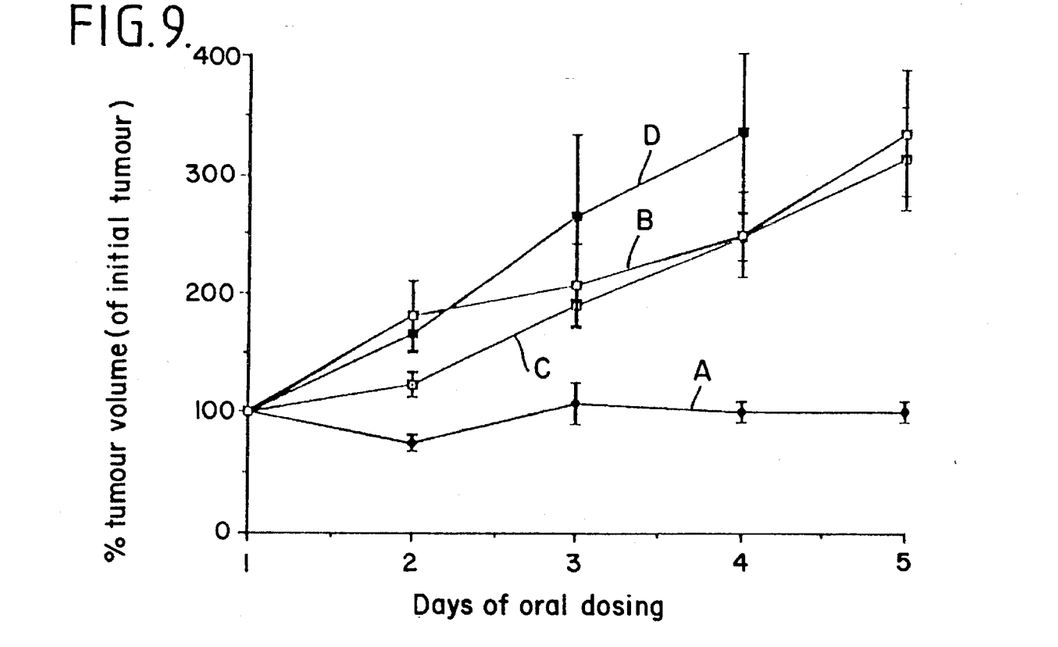
FIGS. 9 and 10 are further diagrams similar to FIGS. 7 and 8 showing additional comparative results.
Figure 10:
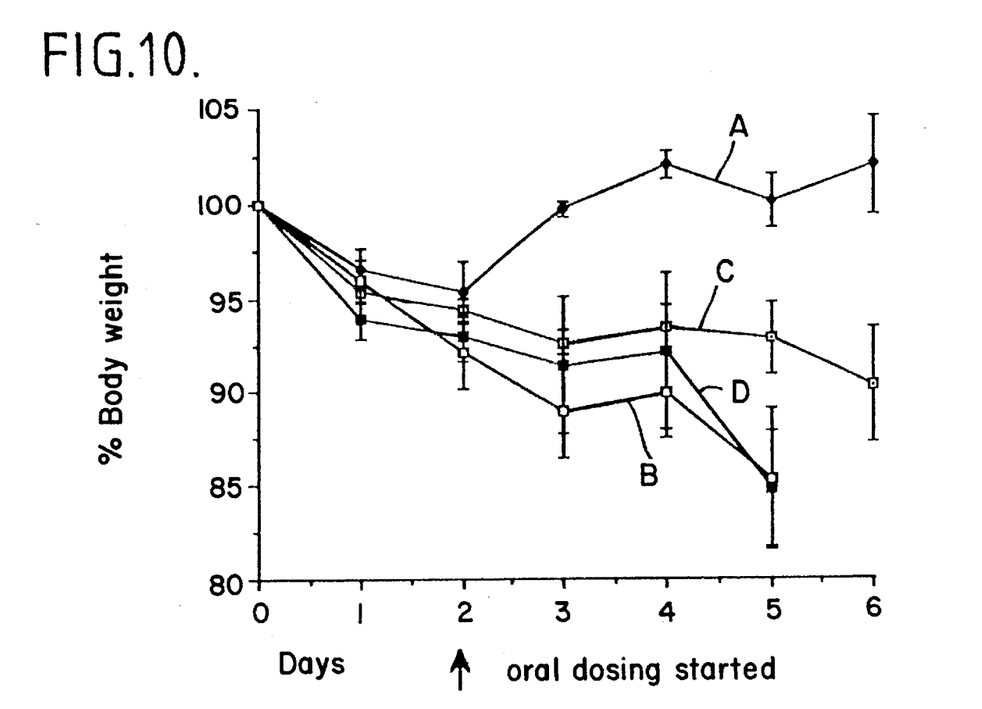

In further experiments, of which the results are shown in FIGS. 9 and 10, the effect of dosing with pure EPA was also compared with the effect of linoleic acid and with that of docosahexaenoic acid (purchased from Sigma Chemical Co., Poole, U.K.), herein referred to shortly as DHA.

FIGS. 9 and 10 shows the results of experiments in which again mice (20 g) were used and dosed orally with either 100 µl EPA/day/mouse (A), 100 µl linoleic acid/day/mouse (B), 100 µl 0.9% saline/day/mouse (C) or 100 µl DHA/day/mouse (D).

The experiment of which the results are shown in FIG. 9 was initiated 14 days after rumour transplantation when the rumours became palpable (average initial rumour volume= 96±12 mm$^3$). Tumour volumes were measured daily and recorded as a percentage of the tumour volume prior to oral dosing. Results are expressed as the mean ±S. E. M.

The effect on host body weight from the treatment relating to FIG. 9 is shown in FIG. 10. The treatment was initiated 14 days after rumour transplanation when weight loss became apparent (average weight loss 7%). Body weights were measured daily and recorded as a percentage of the body weight prior to oral dosing. Results are expressed as the mean±S. E. M. There was no significant difference in food and water intake.

The results presented in these FIGS. 9 and 10 demonstrate clearly that only EPA possesses antitumour and anticachectic activity. In contrast, the related omega-3 polyunsaturated fatty acid DHA, which is also a major constituent of fish oil (18.7%) and which differs from EPA only in the presence of two extra carbon atoms and another double bond, was totally devoid of any antitumour or anticachectic activity, when administered orally at the same dose as EPA (5 g kg$^{-1}$). Moreover, while EPA was non-toxic at this dose level, DHA showed marked signs of toxicity, as evidenced by an increased weight loss compared with the control, and the experiments had to be terminated after only a few oral doses. It has also been ascertained that administration of EPA significantly reduces the level of arachidonic acid (ARA) which appears in the blood plasma of animals bearing the MAC16 tumour However, a similar effect has also been found with administration of DHA, and since only EPA exerts antitumour and anticachectic activity against the MAC16 tumour, this indicates that reductions in rumour ARA, leading perhaps to an inhibition of prostaglandin synthesis, at least in themselves are not of prime importance for either activity.

These results further confirm that in respect of such antitumour and anticachectic effects as have been found, not only is pure EPA even more efficacious and less toxic than anticipated, but EPA appears to have special properties not shared by the other polyunsaturated fatty acids.

Thus, the inhibiting or antagonistic effects found for EPA against lipolytic agents that are known to be physiologically active and often associated with a condition of cachexia and also with tumour growth, such as the newly-identified lipolytic factor produced by MAC16 adenocarcinoma rumours, have demonstrated an unexpected high potential for EPA as a valuable therapeutic agent, especially in the treatment of cachexia and/or rumours in mammals, particularly as such newly-identified lipolytic factor is now known to be associated with many other tumours including, it is believed, many if not most human rumours.

We claim:

1. A method for treating cancer cachexia in a mammal by inhibiting lipolytic activity of lipolytic factors which comprises administering to said mammal in need of such treatment, an effective amount of 5,8,11,14,17 -eicosapentaenoic acid or a pharmaceutically acceptable salt or ester thereof; without the primary aim of said method being the treatment of cancer.

2. The method of claim 1 wherein the EPA 5,8,11,14,17 -eicosapenaenoic acid is of at least 90% purity.

3. The method of claim 1 wherein the EPA 5,8,11,14,17 -eicosapentaenoic acid is about 95% pure.

4. The method of claim 1 wherein the EPA 5,8,11,14,17 -eicosapentaenoic acid is substantially free of any other polyunsaturated fatty acids.

* * * * *